(12) United States Patent
Curry et al.

(10) Patent No.: US 7,698,075 B2
(45) Date of Patent: Apr. 13, 2010

(54) THREE-DIMENSIONAL STRUCTURAL DAMAGE LOCALIZATION SYSTEM AND METHOD USING LAYERED TWO-DIMENSIONAL ARRAY OF CAPACITANCE SENSORS

(75) Inventors: Mark A Curry, Lynnwood, WA (US); Simon D Senibi, Covington, WA (US); David L Banks, Renton, WA (US)

(73) Assignee: The Boeing Company, Chicago, IL (US)

( * ) Notice: Subject to any disclaimer, the term of this patent is extended or adjusted under 35 U.S.C. 154(b) by 1095 days.

(21) Appl. No.: 11/353,443

(22) Filed: Feb. 14, 2006

(65) Prior Publication Data

US 2007/0213943 A1    Sep. 13, 2007

(51) Int. Cl.
*G01B 3/00*   (2006.01)
*G06F 11/00*  (2006.01)

(52) U.S. Cl. .............................. 702/34; 702/35; 702/36; 702/188; 324/765

(58) Field of Classification Search ............. 702/32–38, 702/57–65, 116–123, 182–188; 324/765; 73/718
See application file for complete search history.

(56) References Cited

U.S. PATENT DOCUMENTS

| 4,831,507 | A | * | 5/1989 | Colley et al. ............. 363/21.04 |
| 5,225,959 | A | * | 7/1993 | Stearns ................... 361/283.1 |
| 2006/0254366 | A1 | | 11/2006 | Williamson |
| 2007/0131035 | A1 | * | 6/2007 | Krutz et al. .................. 73/768 |

* cited by examiner

*Primary Examiner*—Eliseo Ramos Feliciano
*Assistant Examiner*—Phuong Huynh
(74) *Attorney, Agent, or Firm*—Harness, Dickey & Pierce, P.L.C.

(57) ABSTRACT

A system and method for detecting damage to a structure is provided. The system includes a voltage source and at least one capacitor formed as a layer within the structure and responsive to the voltage source. The system also includes at least one sensor responsive to the capacitor to sense a voltage of the capacitor. A controller responsive to the sensor determines if damage to the structure has occurred based on the variance of the voltage of the capacitor from a known reference value. A method for sensing damage to a structure involves providing a plurality of capacitors and a controller, and coupling the capacitors to at least one surface of the structure. A voltage of the capacitors is sensed using the controller, and the controller calculates a change in the voltage of the capacitors. The method can include signaling a display system if a change in the voltage occurs.

13 Claims, 5 Drawing Sheets

THREE-DIMENSIONAL STRUCTURAL DAMAGE LOCALIZATION SYSTEM AND METHOD USING LAYERED TWO-DIMENSIONAL ARRAY OF CAPACITANCE SENSORS

STATEMENT OF GOVERNMENT RIGHTS

The invention described herein was made in the performance of work under Subcontract No. 1268619-00 granted by the California Institute of Technology Jet Propulsion Laboratory to The Boeing Company, which was performed under NASA Contract No. NMO0710922 and is subject to the provisions of Section 305 of the National Aeronautics and Space Act of 1958 (72 Stat. 435, 42 U.S.C. 2457.) The U.S. Government has certain rights in this invention.

FIELD

The present disclosure relates to systems for detecting damage to structures from high-velocity impact, and more particularly to three-dimensional structure damage localization using a layered two-dimensional array of capacitance sensors.

BACKGROUND

The statements in this section merely provide background information related to the present disclosure and may not constitute prior art.

Generally, in operation, mobile platforms can be subjected to high-velocity impacts from debris. This is especially so with high-speed mobile platforms, such as jet aircraft. These high-velocity impacts can cause damage to the mobile platform, the extent of which may or may not be readily visually detectable by the crew. Currently, damage detection in mobile platforms is labor intensive and many damage detection apparatuses require a portion of the mobile platform to be disassembled, which is time consuming and costly. In addition, some forms of damage detection may not be compatible with mobile platforms that are composed of certain materials. Many presently available damage detection systems also are unable to be used on jet aircraft while in-flight, which can be undesirable. Such systems require the aircraft to remain at a specified location for maintenance testing, which can result in lost service time for the aircraft if it is ultimately determined that an impact occurrence did not result in any structural damage to the aircraft.

Accordingly, it would be desirable to provide a damage detection system that provides for even more efficient damage detection, and also damage detection that can be used while a mobile is traveling en route to a given destination.

SUMMARY

A system and method for detecting damage to a structure is provided. The system includes a voltage source and at least one capacitor coupled to the structure and responsive to the voltage source. The system also includes at least one sensor responsive to the capacitor to sense a voltage across the capacitor. The system further includes a controller responsive to the sensor to determine if damage to the structure has occurred based on the voltage of the capacitor.

The present teachings further provide a method for non-invasively sensing damage to a structure. The method includes providing a plurality of capacitors and a controller, and integrating the capacitors into at least one surface of the structure. The method also includes sensing voltages across the capacitors with the controller, and calculating a change in the voltages of the capacitors with the controller. The method includes signaling if a change in the overall voltage occurs.

The present teachings also provide a structural component. The structural component includes a structural element, and a capacitor integrated into the structural element. The capacitor forms an integral layer of the structural element. The structural element also includes a sensor electrically coupled to the capacitor for sensing a change in capacitance of the capacitor in the event of an anomaly in the integrity of the structural element. The capacitor within the structural element is placed in communication with a controller for monitoring the sensor and providing an output indicating when the integrity of the structural element has been compromised.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

Figure 1:
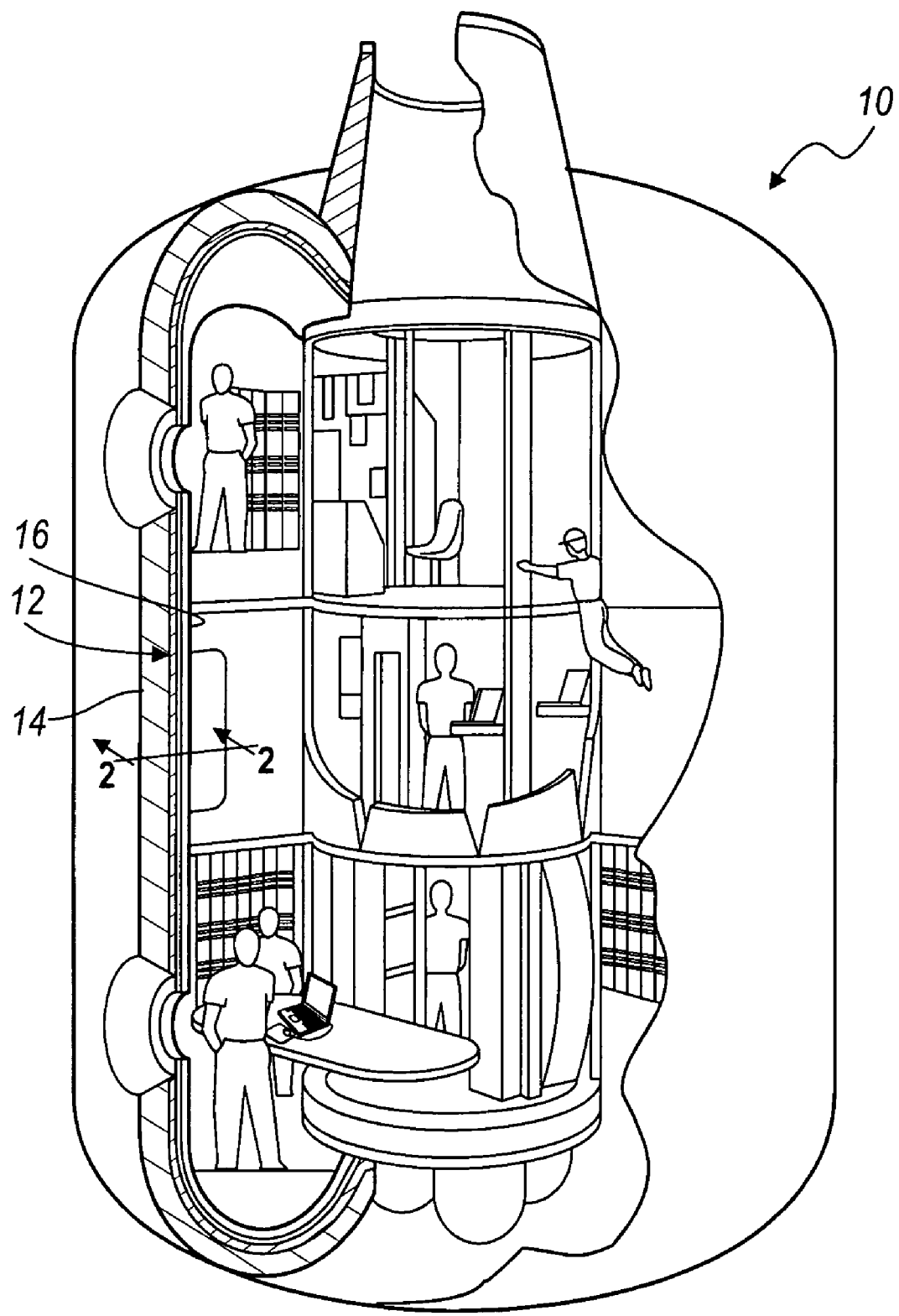
FIG. 1 is a perspective view of an exemplary mobile platform employing a layered two-dimensional array of capacitance sensors.

The following description is merely exemplary in nature and is not intended to limit the present disclosure, application, or uses. It should be understood that throughout the drawings, corresponding reference numerals indicate like or corresponding parts and features.

Although the following description is related generally to structure damage localization using a layered two-dimensional array of capacitance sensors for a mobile platform, such as an aircraft, ship, spacecraft, train or motor vehicle, it will be understood that the damage localization system, as described and claimed herein, can be used with any appropriate application where it would be useful to be able to monitor and detect for structural anomalies in a structure or component, without having to disassemble the structure or component. Therefore, it will be understood that the following discussion is not intended to limit the scope of the appended claims.

With reference to FIG. 1, an exemplary mobile platform 10 employing a damage localization system 12 is shown. The mobile platform 10, in this example, is a spacecraft including a series of outer layers 14 separated from a series of inner layers 16 by the damage localization system 12. With additional reference now to FIG. 2, the damage localization system 12 includes at least one or a plurality of capacitive sensor arrays 18 disposed between pairs of structural elements, pairs of protective shielding 20, or various combinations thereof. The capacitive sensor arrays 18 and protective shielding 20 can generally be sandwiched between the series of outer layers 14 and the series of inner layers 16. The capacitive sensor arrays 18 are coupled to the protective shielding 20 through any appropriate fastening mechanism, such as mechanical fasteners, adhesive bonding or welding, or could be integrally formed with the protective shielding 20 (not specifically shown). With additional reference to FIG. 3, a control system 22 is in communication with each of the capacitive sensor arrays 18 to determine if an anomaly in the integrity of the outer layers 14 and/or protective shielding 20 has occurred, which thereby compromises the integrity of the outer layers 14 and/or protective shielding 20, as a result of puncture damage from an impact with a meteoroid in space. A display system 24 (FIG. 5) coupled to the control system 22 can notify an operator (not specifically shown) of the mobile platform 10 that such damage has occurred, as will be discussed in greater detail herein in conjunction with FIG. 5.

Figure 2:
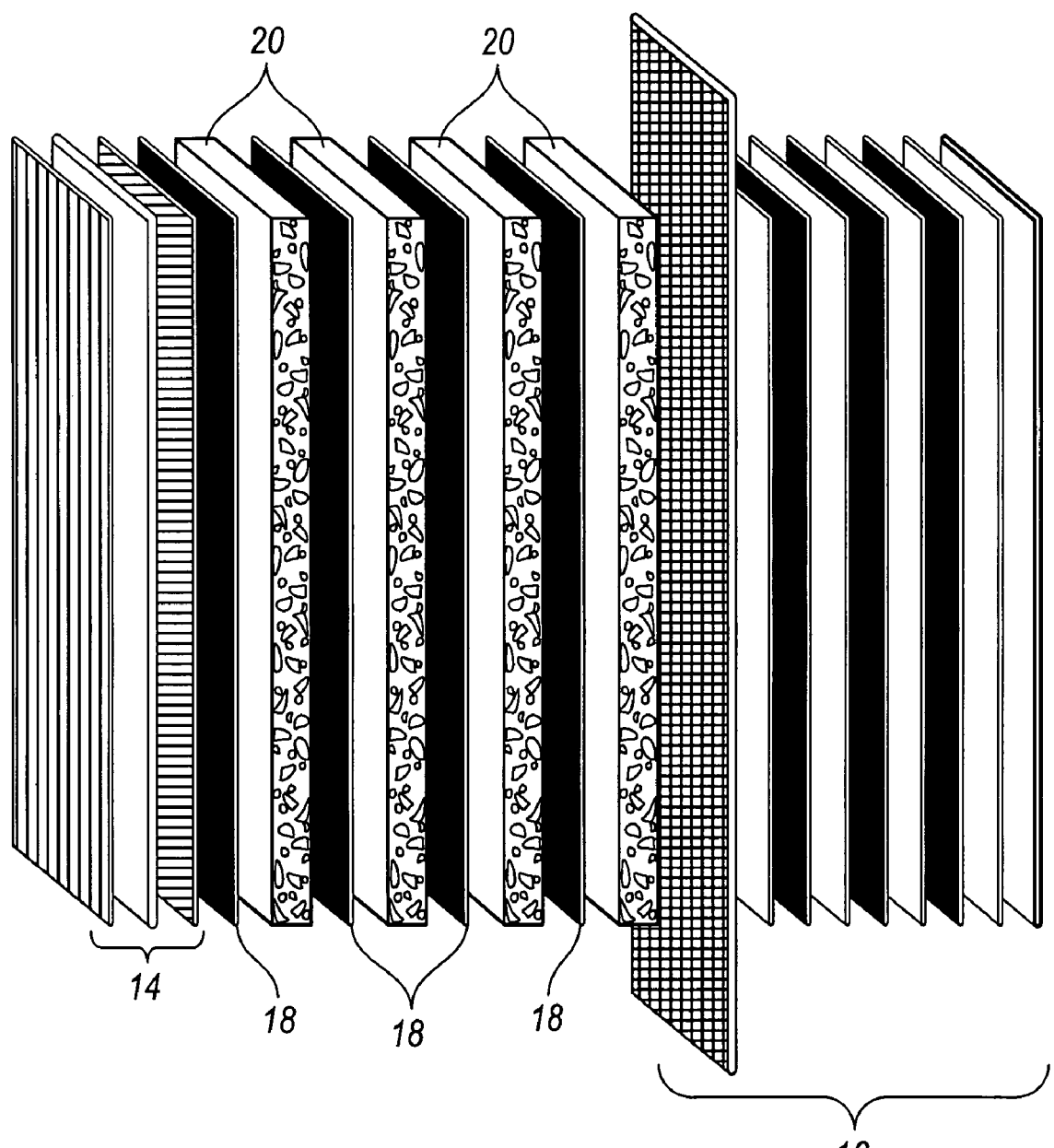
FIG. 2 is a cross-sectional view of the mobile platform of FIG. 1, taken along line 2-2 in FIG. 1, illustrating, in exploded perspective fashion, the layered two-dimensional array of capacitance sensors arranged within the structure of the mobile platform.
Figure 3:
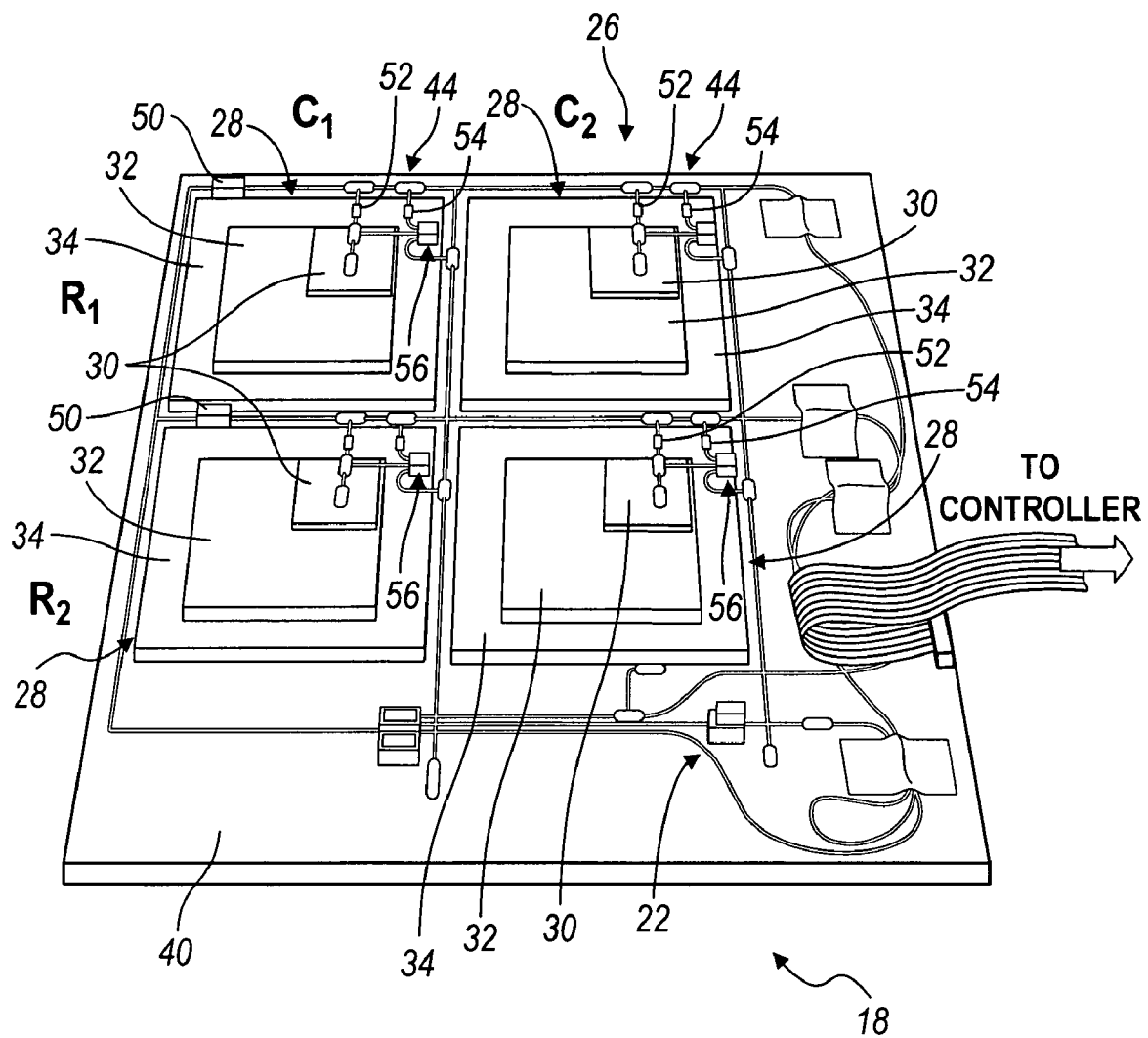
FIG. 3 is a detailed perspective view of a portion of the layered two-dimensional array of capacitance sensors and a system for monitoring the layered two-dimensional array of capacitance sensors.

With continuing reference to FIGS. 1, 2 and 3, the capacitive sensor arrays 18 include a capacitor grid 26 including a plurality of capacitors 28 each in communication with a ground 40 and the control system 22. As each of the capacitive sensor arrays 18 are substantially similar, only a portion of a capacitor grid 26 of one capacitive sensor array 18 will be discussed herein. Generally, the capacitors 28 are parallel plate capacitors having at least a pair of plates, and more preferably three or more parallel plates. In this example, the capacitors 28 include a first layer 30, a second layer 32, a third layer 34, a fourth layer 36 and a fifth layer 38, as further shown in FIG. 4. The first layer 30 can be composed of the same material as the fifth layer 38, which is a conductive material, such as copper or aluminum. The thickness of the first layer 30 and the fifth layer 38 can range from about 0.01 mil to about 2.0 mils (~0.000254-0.0508 mm), but more preferably is about 0.5 mil (~0.0127 mm).

The second layer 32 and fourth layer 36 are each composed of a dielectric material, and is disposed between the first layer 30 and the fifth layer 38. Generally, the dielectric material employed is flexible for ease in manufacturing, such as KAPTON® polyimide film manufactured by DuPont. The thickness of each of the second layer 32 and the fourth layer 36 preferably ranges from about 0.01 mil to about 4.0 mils (~0.000254-0.1016 mm), but is more preferably about 3.0 mils (~0.0762 mm) thick. The first layer 30, second layer 32, fourth layer 36 and fifth layer 38 form a first electrode of the capacitor 28 that is coupled to a resistor 39 which is coupled to ground 40. The resistor 39 sets the input impedance into the controller 48.

Figure 4:
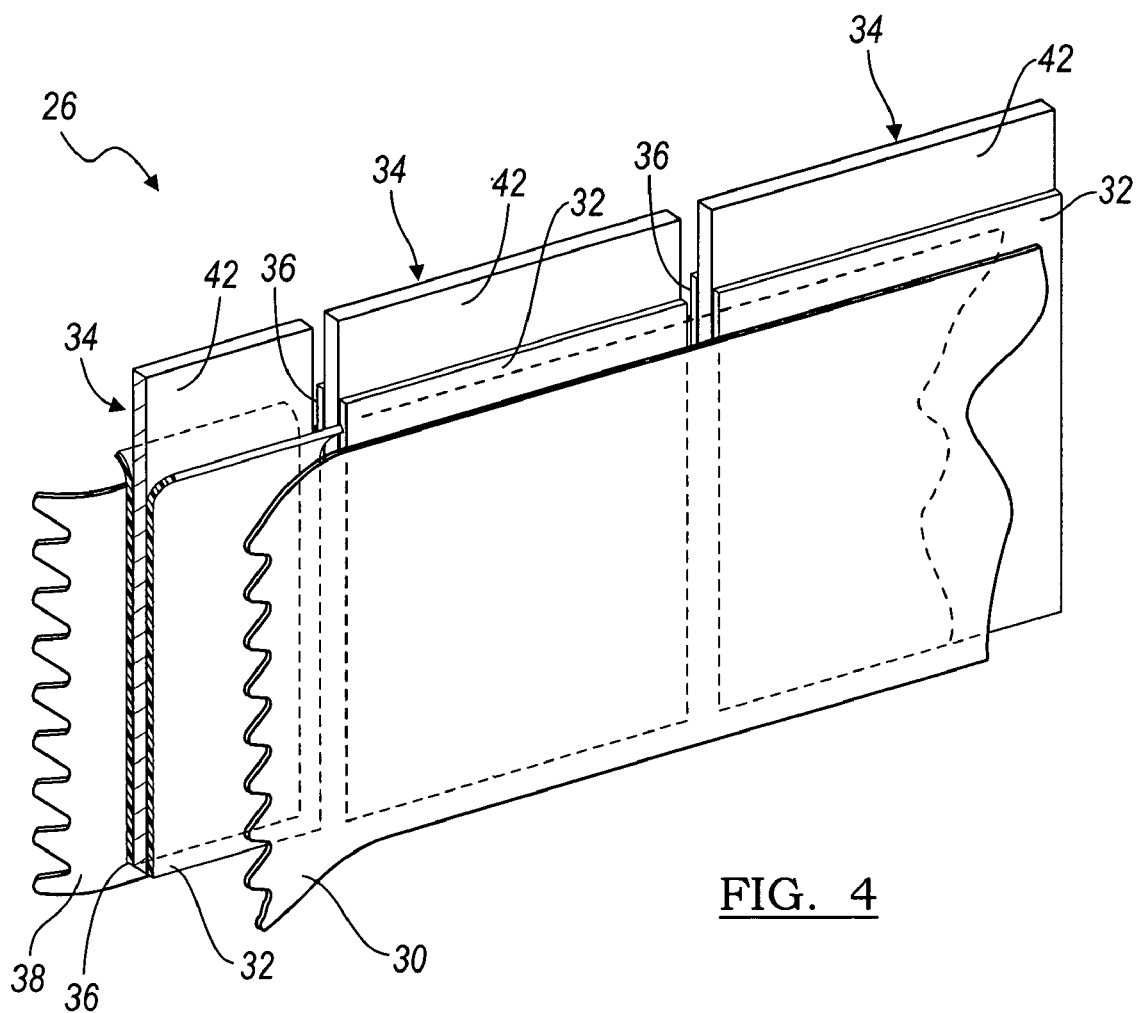
FIG. 4 is a detailed side perspective view of the capacitive sensor grid of FIG. 3 showing the exemplary layers of the capacitor.

The third layer 34 forms a second electrode of the capacitor 28 that is in communication with the control system 22. The third layer 34 is composed of a conductive material, such as copper or aluminum, and is disposed between the second layer 32 and the fourth layer 36. The thickness of the third layer 34 can range from about 0.01 mil to about 2.0 mils (~0.000254-0.0508 mm), but more preferably is about 1.0 mil (~0.0254 mm). A section 42 of the third layer 34 extends beyond the first, second, fourth and fifth layers 30, 32, 34, 36 and 38 to enable each of the capacitors 28 to be electrically coupled to the control system 22 (FIG. 4). The first, second, third, fourth and fifth layers 30, 32, 34, 36 and 38 are coupled together through any suitable technique, such as spray adhesives, adhesive tape or other bonding techniques (not specifically shown).

The capacitor grid 26 is arranged with capacitors 28 forming rows R1, R2 . . . Rn and columns C1, C2 . . . Cn. Each of the rows R and columns C form conductive circuit traces that make up a grid for the control system 22. This arrangement of the capacitors 28 enables each capacitor 28 to provide a discrete input to the control system 22 for the determination of damage to the particular region defined by the row R and column C of the capacitor 28.

Figure 5:
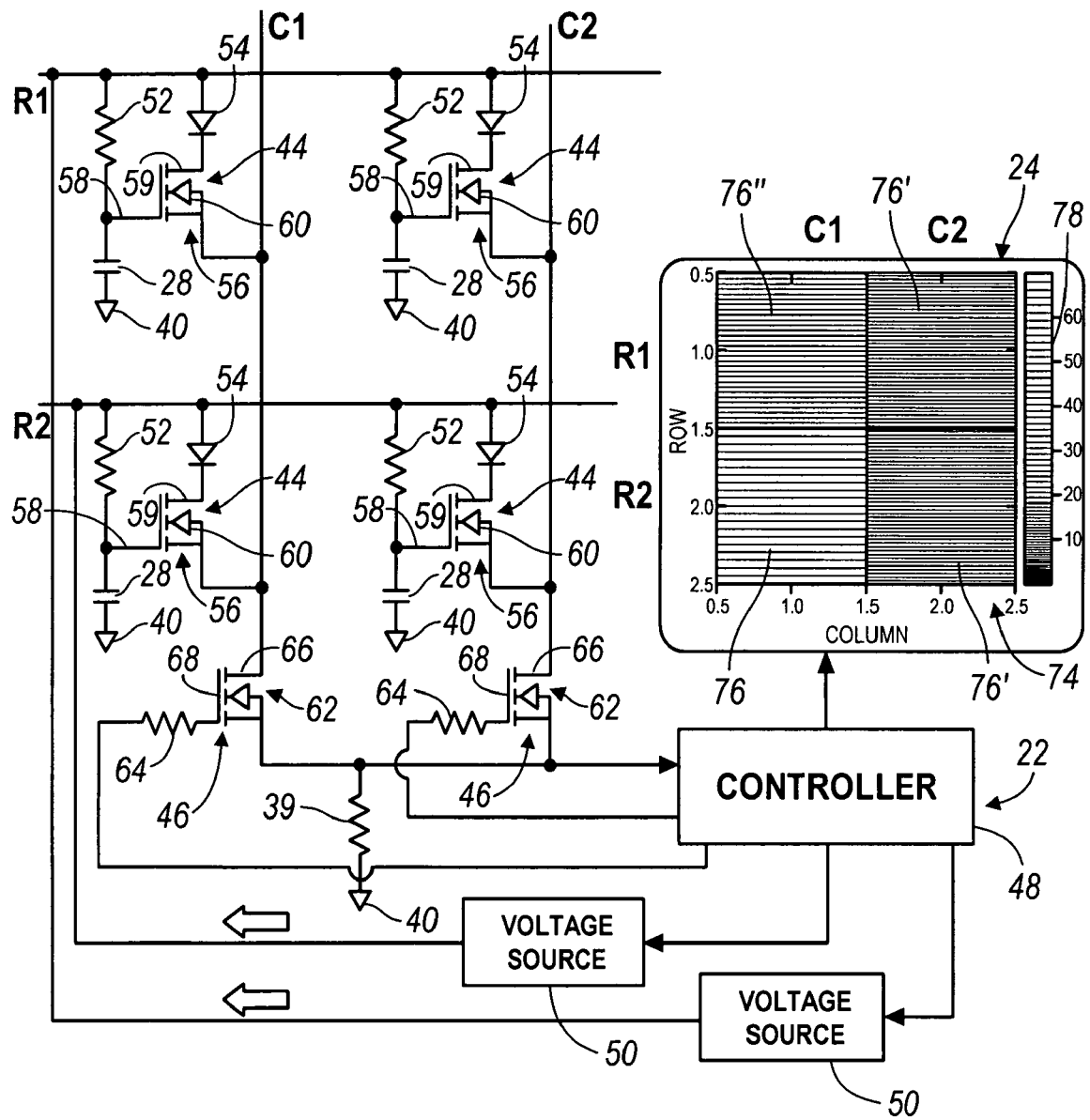
FIG. 5 is an exemplary schematic diagram of the capacitive sensor array of FIG. 2 including the control system.

The control system 22 can determine if damage has occurred to a specific capacitor 28 in the capacitor grid 26. The control system 22 includes at least one or a plurality of sensor systems 44, an output sensor system 46, a controller 48, and voltage sources 50 that are coupled to the capacitors 28 in a particular row R1, R2 . . . Rn of the capacitor grid 26, as best shown in FIGS. 3 and 5. The control system 22 is identical for each of the capacitive sensor arrays 18, and thus the control system 22 will be described herein as applied to one portion of the capacitor grid 26 of one capacitive sensor array 18. It will be understood that the control system 22, as described herein, could be modified as necessary to interact with various layers of capacitive sensor arrays 18.

Each capacitor 28 in the capacitor grid 26 includes an associated sensor system 44 that is in communication with the third layer 34 of each capacitor 28. Each of the sensor systems 44 is also in communication with the conductive row R and column C associated with the particular capacitor 28, as best shown in FIG. 5. A separate one of the voltage sources 50 is coupled to each sensor system 44, and can be turned on and off independently by the controller 48. The sensor system 44 includes a resistor 52, a diode 54 and a transistor 56, which, in this example, is an N-channel metal-oxide semiconductor field-effect transistor (MOSFET).

The resistor 52 is in communication with a particular row R and with the third layer 34 of the capacitor 28 to enable current to flow to the capacitor 28. The resistor 52 has a resistance of about 10 kilohms; however, this value can be varied as needed to suit an application. The diode 54 is in communication with a particular row R to control the flow of current in the particular row R to one direction only, and to maximize the sensitivity of the row R.

The MOSFET 56 of a particular sensor system 44 is in communication with the diode 54 and a selected capacitor 28. The MOSFET 56 has its gate 58 in communication with the capacitor 28. A drain 59 is in communication with the diode 54, and a source 60 is in communication with the output sensor system 46 through a selected column C. The MOSFET 56 associated with each capacitor 28 can act as a buffer to isolate the capacitor 28 from the other capacitors 28 in the capacitor grid 26, thus maximizing the sensitivity of the capacitive sensor array 18. The gate 58 of the MOSFET 56 receives the voltage from the capacitor 28. The voltage from the capacitor 28 is used to determine if the mobile platform 10 has been damaged, as will be discussed in greater detail herein. The voltage from the capacitor 28 is used to turn on the MOSFET 56 to enable a current signal to be sent to the output sensor system 46, and then to the controller 48 through the source 60 of the MOSFET 56.

The output sensor system 46 is in communication with each MOSFET 56 on an associated column C through the source 60 of each MOSFET, and in communication with the controller 48. The output sensor system 46 includes a MOSFET 62 and a biasing resistor 64. The MOSFET 62 includes a first drain 66 in communication with the column C1, C2 . . . Cn for receiving the voltage across the selected capacitor 28 in the column C1, C2 ... Cn, and a gate 68 in communication with the resistor 64, which is in turn in communication with the controller 48. The resistor 64 has a resistance of about 1 kilohm. The resistor 64 serves to increase the sensitivity and accuracy of the output signal from the MOSFETs 62. The controller 48 applies a signal to the gate 68 of a selected one of the MOSFETs 62 to turn it on at a predetermined time when its associated capacitor 28 is being checked. All of the other MOSFETs 62 are held in an "off" condition during this time. This enables one selected capacitor 28 at a time to be analyzed by the controller.

The controller 48 is in communication with each of the output sensor systems 46 of the columns C1 to Cn. The controller 48 is preferably a microcontroller and may include an analog-to-digital (A/D) converter; however, any suitable controller could be used. The gate 68 of the MOSFET 62 is in communication with the controller 48 so that the controller 48 can enable the current flowing through the circuit line C1, and thus the voltage associated with the capacitors 28 in column C, to be measured when its associated voltage source 50 is turned on by the controller 48.

The voltage source 50 provides five volts (V) to the selected row R of capacitors 28. The voltage source 50 can be any temperature compensated voltage reference. After the particular voltage source 50 for a row R has been activated to charge the particular row R of capacitors 28, the controller 48 queries the output sensor systems 46, one at a time, to determine the voltage on each of the capacitors 28. The controller 48 is in communication with the display system 24 to visually inform the operators of the mobile platform 10 if there has been any damage to any of the protective shielding 20 based on the signal from the output sensor systems 46 for each of the particular columns C1 to Cn.

The display system 24 can provide operators on the mobile platform 10 with data regarding damage to the mobile platform 10 based on the data received from the controller 48. The display system 24 includes a display 74 in communication with the controller 48 for receipt of data associated with a particular row R and column C of the capacitor grids 26. The data from the controller 48 is displayed in a grid format with each box 76 associated with a particular capacitor 28 of a particular capacitive sensor array 18. A color scale 78 is used to indicate if any of the capacitors 28 are damaged. For illustration purposes only, the color scale 78 can be such that undamaged areas are a lighter color than damaged areas. The amount of damage to a particular capacitor 28 can also be illustrated by the color intensity of the particular box 76. For example purposes only, the capacitor 28 illustrated as box 76' has a 2.0 mm (~0.079 inch) hole, while the capacitor 28 illustrated as box 76" has a 1.0 mm (~0.039 inch) hole, as shown by the darker shade associated with the box 76'.

In order to determine the amount of damage to the capacitor 28, first the capacitor grid 26 is assembled such that each capacitor 28 in the capacitor grids 26 is in communication with an associated sensor system 44. Then, the output sensor systems 46 are placed in communication with each column C of the multiple capacitor grids 26. Next, each voltage source 50 is placed in communication with the particular rows R1, R2...Rn of the multiple capacitor grids 26. The output sensor systems 46 and the voltage sources 50 are then coupled to the controller 48. Each of the capacitor grids 26 can then be layered between the protective shielding 20 at the desired intervals.

In order to detect if damage has occurred to the protective shielding in front of the capacitor grid 26, the controller 48 queries each of the capacitor grids 26 to determine if any of the capacitors 28 have been damaged. Damage to the capacitors 28 is highly likely to indicate damage to the protective shielding 20 disposed in front of a given capacitor 28. Damage to the capacitors 28 is determined by an increase in voltage (V) of the capacitor 28. More specifically, if a capacitor 28 has been damaged, the capacitance of the capacitor 28 will change. The capacitance of the capacitor 28 in an uncompromised or undamaged position is approximately 175 pico-Farads (pF). Generally, the capacitance of the capacitor 28 is given by:

$$C = \frac{\varepsilon_r \varepsilon_0 S}{d} \quad (1)$$

wherein S is the surface area, d is the plate spacing, and $\varepsilon_r$ is the relative dielectric constant (the dielectric constant for KAPTON® polyimide film is approximately 3.1).

When damage occurs to the capacitor 28, the puncture will remove some of the surface area S of the capacitor 28, causing a reduction in the capacitance of the capacitor 28. However, one suitable way to measure the change in capacitance of the capacitor 28 is by measuring the change in voltage $\Delta V$ of the capacitor 28. First, starting with the capacitor current given by:

$$i_c = C \frac{\Delta V}{\Delta t} \quad (2)$$

wherein $\Delta V$ is the change in voltage in volts (V) and $\Delta t$ is the change in time t in seconds (sec), and then inserting equation (1) into equation (2), and solving for the change in voltage, $\Delta V$ yields:

$$\Delta V = \frac{i_c d \Delta t}{\varepsilon_r \varepsilon_0 S} \quad (3)$$

Thus, as the change in voltage is inversely proportional to the surface area S of the capacitor 28, and as the area S decreases, the voltage V of the capacitor 28 increases with the capacitor current, charging time, and plate spacing held constant. In order to determine the appropriate size of the capacitor 28 for sensing a reduction in surface area S, a small damage area s can be subtracted from the surface area S in equation (3) to arrive at:

$$\Delta V = \frac{i_c d \Delta t}{\varepsilon_r \varepsilon_0} \left( \frac{1}{S_0 - s} \right) \quad (4)$$

wherein $S_0$ is the surface area of the undamaged capacitor 28 and s is the damaged area. Solving for $\Delta$ yields:

$$\Delta = \frac{S_0}{S_0 - s} \quad (5)$$

Thus, $\Delta$ can be maximized when the undamaged surface area $S_0$ of the capacitor 28 is not too large relative to the damaged area s of the capacitor 28. Thus, in order to most effectively measure a small change in voltage of the capacitor 28 (approximately 0.1% change), the ratio of the undamaged surface area $S_0$ to the damaged area s of the capacitor 28 should be greater than 0.001. Generally then, the capacitors 28 can be about 1 inch by 1 inch (~2.54×2.54 cm) patches. It will be appreciated, however, that the specific shape and dimensions of the capacitors 28 may vary to suit the needs of specific applications.

In order to determine if any of the capacitors 28 have been punctured, the controller 48 sends a signal to the particular voltage source 50 to energize a particular row R of capacitors 28 in a particular capacitive sensor array 18. In the example of FIG. 5, the controller 48 has the voltage source 50 energize the row R of capacitors 28 at 5V for 2 microseconds (μs). This causes a voltage to be applied to the gates 58 of each MOSFET 56 as is associated capacitor 28 charges. The controller 48 can then apply a signal to the gate 68 of the MOSFET 62 of a specific one of the output sensor systems 46 to turn it on. As only one of the MOSFETs 62 is energized at a time, each MOSFET 62 can provide the controller 48, through its associated MOSFET 62, with a discrete signal. This signal enables the controller 48 to precisely determine the capacitance of a specific one of the capacitors 28 in the capacitor grid 26 of the particular capacitive sensor array 18, and transmit that information to the display system 24.

Based on the voltage detected from the capacitor 28, the controller 48 transmits a signal to the display system 24 to illuminate the box 76 in the display 74 associated with the particular capacitor 28. If the voltage V associated with the particular capacitor 28 is substantially equivalent to a voltage expected from an undamaged capacitor 28, then the controller 48 sends a signal to the display system 24 to illuminate the box 76 associated with the particular capacitor 28 according to the color scale 78 for an undamaged capacitor 28. For example, the undamaged capacitor 28 can be shown as a light gray color, as indicated in box 76.

If, however, the voltage V of the capacitor 28 is greater than the voltage expected with an undamaged capacitor 28, then the controller 48 sends a signal to the display system 24 to illuminate the box 76 associated with the damaged capacitor 28 as a darker or more intense shade of color, depending on the color scale 78. For example, the damaged capacitor 28 can be shown as a darker gray box 76'. The controller 48 performs the above procedure for each of the capacitive sensor arrays 18 at time intervals defined by the application employing the capacitive sensor arrays 18 to enable the operators of the mobile platform 10 to check each of the capacitive sensor arrays 18 as desired. It will be noted, however, that the controller 48 could query each of the capacitive sensor arrays 18 and display the results on a larger display or on a three-dimensional display (not shown). Thus, based on the shading of the boxes 76 in the display 74, the operators of the mobile platform 10 can determine if the mobile platform 10 has been damaged.

While various preferred embodiments have been described, those skilled in the art will recognize modifications or variations which might be made without departing from the inventive concept. The examples illustrate the invention and are not intended to limit it. Therefore, the description and claims should be interpreted liberally with only such limitation as is necessary in view of the pertinent prior art.

What is claimed is:

1. A system for detecting damage to a structure comprising:
at least one voltage source;
a plurality of capacitors arranged in a grid formation of rows and columns, and each said capacitor being responsive to a signal from the voltage source;
a plurality of output sensors responsive to each said column of the capacitors to sense a voltage of each one of the capacitors;
a controller responsive to the output sensors to query each said output sensor sequentially to determine if damage to one or more areas of the structure has occurred based on the sensed voltages and wherein the voltage source responsive to the controller to energize a specific row of the plurality of capacitors.

2. The system of claim 1, each of the capacitors comprising a parallel plate capacitor.

3. The system of claim 2, each of the capacitors comprising a polyimide film capacitor having layers 0.01 mil to 3.0 mils thick.

4. The system of claim 1, each of the capacitors having a capacitance of 175 picoFarads when the structure is undamaged.

5. The system of claim 1, each of the capacitors having a capacitance of less than 175 picoFarads if damage to the structure has occurred.

6. The system of claim 1, further comprising:
a display system coupled to the controller, the display system responsive to the controller to notify an operator of the mobile plafform that damage has occurred to the structure.

7. The system of claim 1, the controller adapted to query a column of the output sensors after the voltage source has energized the row of the plurality of capacitors.

8. The system of claim 1, one of said capacitors having an increased voltage if damage has occurred to the structure in an immediate vicinity of said one of the capacitors.

9. A method for sensing damage to a structure comprising:
providing a plurality of capacitors;
coupling the capacitors to at least one surface of the structure;
arranging the capacitors in a grid;
energizing a row of capacitors in the grid with a voltage for a predetermined time;
sensing a voltage across a column of capacitors in the grid;
using a controller to detect if the sensed voltage across the column deviates from a predetermined reference value for the row of capacitors illuminating the area of a display system comprises illuminating the area with one of a predetermined shading and color; and increasing the intensity of the shading of the area based on an amount of detected damage to a given one of capacitors.

10. The method of claim 9, further comprising:
providing a display system responsive to the controller; and
transmitting a signal to the display system to indicate if any of the capacitors have been damaged, the display system illuminating an area thereof corresponding to a given one of the capacitors to denote whether said given one of the capacitors has been damaged.

11. A structural component comprising:
a structural element;
a plurality of capacitors arranged in a grid of rows and columns of the capacitor;
a plurality of output sensors responsive to each said column of the capacitors for sensing a change in capacitance of each of the capacitors in the event of an anomaly in the integrity of the structural element;
a controller for querying each one of the output sensors sequentially and providing an output indicating when the integrity of the structural element has been compromised and a voltage source responsive to the controller to energize a row of the plurality of capacitors, the controller adapted to receive a signal from a column of the output sensors after the voltage source has energized the row of the plurality of capacitors, said signal being indicative of a capacitance of said column of capacitors.

12. The structural component of claim 11, further comprising:
a display system responsive to the output of the controller to notify an individual that the structure is compromised.

13. The structural component of claim 11, the structural element comprising a plurality of layers with the grid comprising the plurality of capacitors disposed in-between the plurality of layers.

* * * * *